US012685706B2

(12) United States Patent
Liang et al.

(10) Patent No.: US 12,685,706 B2
(45) Date of Patent: Jul. 21, 2026

(54) OIL-IN-WATER EMULSION AND USE THEREOF

(71) Applicant: WACKER CHEMIE AG, Munich (DE)

(72) Inventors: Xinyu Liang, Shanghai (CN); Yuwen Liang, Shanghai (CN)

(73) Assignee: Wacker Chemie AG, Munich (DE)

( * ) Notice: Subject to any disclaimer, the term of this patent is extended or adjusted under 35 U.S.C. 154(b) by 720 days.

(21) Appl. No.: 17/767,074

(22) PCT Filed: Oct. 25, 2019

(86) PCT No.: PCT/CN2019/113223
§ 371 (c)(1),
(2) Date: Apr. 7, 2022

(87) PCT Pub. No.: WO2021/077387
PCT Pub. Date: Apr. 29, 2021

(65) Prior Publication Data
US 2022/0362133 A1 Nov. 17, 2022

(51) Int. Cl.
| | |
|---|---|
| *C08L 83/08* | (2006.01) |
| *A61K 8/06* | (2006.01) |
| *A61K 8/89* | (2006.01) |
| *A61K 8/898* | (2006.01) |
| *A61Q 5/06* | (2006.01) |
| *C08L 83/04* | (2006.01) |
| *C08L 83/06* | (2006.01) |

(52) U.S. Cl.
CPC .............. *A61K 8/898* (2013.01); *A61K 8/062* (2013.01); *A61K 8/89* (2013.01); *A61Q 5/06* (2013.01); *C08L 83/04* (2013.01); *C08L 83/06* (2013.01); *C08L 83/08* (2013.01)

(58) Field of Classification Search
CPC ................................ C08L 83/08; A61K 8/062
See application file for complete search history.

(56) References Cited

U.S. PATENT DOCUMENTS

| | | | |
|---|---|---|---|
| 6,180,117 B1 | 1/2001 | Berthiaume et al. | |
| 6,737,444 B1 | 5/2004 | Liu | |
| 7,319,119 B2 | 1/2008 | Mahr et al. | |
| 2006/0041026 A1 | 2/2006 | Mahr et al. | |
| 2016/0235654 A1 | 8/2016 | Herrlein et al. | |
| 2017/0252287 A1 | 9/2017 | Zhang et al. | |
| 2020/0179246 A1* | 6/2020 | Liang ..................... A61K 8/062 | |

FOREIGN PATENT DOCUMENTS

| | | |
|---|---|---|
| CN | 1737061 A | 2/2006 |
| EP | 2431421 A1 | 3/2012 |
| EP | 3058933 B1 | 6/2018 |
| JP | 5863802 B2 | 2/2016 |
| WO | 2015082358 A1 | 6/2015 |
| WO | 2018218417 A1 | 12/2018 |

* cited by examiner

*Primary Examiner* — Margaret G Moore

(57) ABSTRACT

An oil-in-water emulsion which includes one or more amino polyorganosiloxanes (A1), one or more silicone resins (A2), a surfactant composition (B) and water. The oil-in-water emulsion forms a film having a higher degree of crosslinking and an improved strength. Additionally, the oil-in-water emulsion is usable within hair care products to make hairstyles hold and offer a smooth, non-sticky hand feel. Furthermore, the oil-in-water emulsion also has good storage stability.

18 Claims, No Drawings

OIL-IN-WATER EMULSION AND USE THEREOF

CROSS-REFERENCE TO RELATED APPLICATIONS

This application is a U.S. National Phase application of PCT Application No. PCT/CN2019/113223 filed on Oct. 25, 2019 the disclosure of which is incorporated by reference herein in its entirety.

FIELD OF THE INVENTION

The present invention relates to a film-forming oil-in-water emulsion and use thereof in personal care products.

BACKGROUND OF THE INVENTION

An oil-in-water emulsion refers to a dispersion system in which the discontinuous oil phase is dispersed as droplets in a continuous aqueous phase, wherein the oil droplets are generally spherical or almost spherical, and typically covered by a surfactant. It is known that according to the particle size and appearance, emulsions can be classified into: standard, mini- and micro-emulsions. Standard emulsions have a relatively large particle size (typically greater than 300 nm) and are opaque to the human eye with a milky white appearance. Miniemulsions have a relatively small particle size and are visually observed to have a blue-white to translucent appearance. Microemulsions have a transparent appearance, making it suitable for producing highly transparent products, and they are the most stable against phase separation or sedimentation.

Emulsions of amino polyorganosiloxanes and high molecular weight silicones are widely used in hair care compositions. Various types of emulsions have been commercially developed to provide water-based products containing such silicone oils for use as hair conditioners.

U.S. Pat. No. 6,737,444B1 discloses a method for making an oil-in-water emulsion, wherein an amino polyorganosiloxane and a silicone resin are mixed to form a homogeneous oil phase, to which a surfactant composition is added to obtain a homogeneous mixture, and then water is added to the mixture to cause phase inversion to form an opaque oil-in-water emulsion having a particle size in the range of from 100 to 5,000 nm.

U.S. Pat. No. 6,180,117B1 discloses a process for preparing emulsions of aminomethyl silicone fluid and silicone resin mixtures, wherein an oil phase containing the silicone resin is mixed at room temperature with a selected surfactant composition having a specific phase inversion temperature and heated to 70° C., and, while heating, the first portion of water, acid and the second portion of water are added to obtain an oil-in-water emulsion having a particle size ranging from 5 to 50 nm and a turbidity of less than 150.

U.S. Pat. No. 7,319,119B2 discloses a process for preparing emulsions by mixing a low-viscosity amino-functional silicone oil with a silicone resin.

WO2018218417A1 discloses a microemulsion comprising liquid amino polyorganosiloxanes and silicone resins. When a low-viscosity amino polyorganosiloxane is selected, the microemulsion can form a uniform solid film, which however has a low strength and is prone to breakage under an external force.

SUMMARY OF THE INVENTION

The present invention intends to obtain a new oil-in-water emulsion which, upon drying at room temperature, forms a film having a higher degree of crosslinking and an improved strength. It can be used in hair care products to make hairstyles hold and offer a smooth, non-sticky hand feel. The novel emulsion also has good storage stability.

A film-forming oil-in-water emulsion comprising one or more amino polyorganosiloxanes (A1), one or more silicone resins (A2), a surfactant composition (B) and water, wherein at least 80 mol % of units of the amino polyorganosiloxanes (A1) are selected from those having the following general formulas Ia, Ib II and III:

$$R^1_2SiO_{(4-a-b)/2} \tag{Ia}$$

$$R^1_aR^2_bSiO_{(4-a-b)/2} \tag{Ib}$$

$$R^3_3SiO_{(1/2)} \tag{II}$$

$$R^3_2R^4SiO_{(1/2)} \tag{III}$$

where
a has the value 0 or 1, b has the value 1 or 2, and a+b is equal to 2;
$R^1$ represents monovalent hydrocarbon groups having 1-40 carbon atoms;
$R^2$ represents aminoalkyl groups of the general formula IV:

$$-R^5-NR^6R^7 \tag{IV}$$

where $R^5$ represents divalent hydrocarbon groups having 1-40 carbon atoms,
$R^6$ represents divalent hydrocarbon groups having 1-40 carbon atoms, H, hydroxymethyl or alkanoyl, and
$R^7$ represents groups of the general formula V:

$$-(R^8-NR^6)_xR^6 \tag{V}$$

where x is 0 or an arbitrary integer from 1 to 40, and $R^8$ represents divalent groups of the general formula VI:

$$-(CR^9_2-)_y \tag{VI}$$

where y an arbitrary integer from 1 to 6, and $R^9$ represents H or hydrocarbon groups having 1-40 carbon atoms;
$R^3$ represents optionally halogen-substituted hydrocarbon groups having 1-40 carbon atoms;
$R^4$ represents —OR or —OH groups; and
(Ia+Ib)/(II+III), meaning the average ratio of the sum of units of the general formulas Ia and Ib to the sum of units of the general formulas II and III, ranges from 0.5 to 1000, wherein II/III≤1, preferably II/III≤0.9, more preferably II/III≤0.5, even more preferably II/III≤0.3, most preferably II/III=0;
and the amino polyorganosiloxanes (A1) have a viscosity of from 3,000 to 9,000 mPa·s, more preferably from 3,000 to 7,000 mPa·s, most preferably from 4,000 to 6,000 mPa·s; and wherein at least 80 mol % of units of the silicone resins (A2) are selected from those having the following general formulas VII, VIII, IX and X:

$$R^{10}_3SiO_{(1/2)} \quad \text{(VII)}$$

$$R^{10}_2SiO_{(2/2)} \quad \text{(VIII)}$$

$$R^{10}SiO_{(3/2)} \quad \text{(IX)}$$

$$SiO_{(4/2)} \quad \text{(X)}$$

where $R^{10}$ represents hydrocarbon groups that have 1-40 carbon atoms and are optionally substituted by halogens, or H, —OR or —OH groups, at least 20 mol % of the units are selected from those having the general formulas IX and X, and at most 30 wt % of $R^{10}$ are —OR and/or —OH groups, based on the total weight of the silicone resins (A2).

The "film-forming" oil-in-water emulsion of the present invention refers to an emulsion that how it forms a film and the degree of film formation are defined in the section "Film-forming Experiment" herein. A film having a higher degree of crosslinking and an improved strength refers to a case where the score is greater than or equal to 2 in Table 3, preferably greater than or equal to 3.

According to the emulsion mentioned above, in the terminal groups of the amino polyorganosiloxanes (A1) the number of moles of hydroxyl groups is greater than that of alkoxy groups.

According to the emulsion mentioned above, the amino polyorganosiloxanes (A1) have an amine number of greater than or equal to 0.01 meq/g, preferably greater than or equal to 0.05 mmol/g, more preferably greater than or equal to 0.1 mmol/g.

According to the emulsion mentioned above, the silicone resins (A2) are mainly MQ type resins, of which at least 80 mol % of units, preferably at least 90 mol %, more preferably at least 95 mol % are selected from those having the general formulas VII and X, based on the total units of the silicone resins (A2) as 100 mol %.

According to the emulsion mentioned above, the silicone resins (A2) have an M/Q ratio of from 0.5 to 0.7.

According to the emulsion mentioned above, the silicone resins (A2) contain the phenyl groups in an amount of 10 wt %, preferably less than 5 wt %, more preferably less than 1 wt %, based on the total weight of A2.

According to the emulsion mentioned above, the silicone resins (A2) have a weight average molecular weight (Mw) of greater than or equal to 2,000 g/mol, preferably from 2,000 to 20,000 g/mol, more preferably from 2,000 to 10,000 g/mol, most preferably from 5,000 to 8,000 g/mol.

According to the emulsion mentioned above, the silicone resins (A2) are solid at 25° C. and 1 atm.

The emulsion mentioned above optionally comprises a low-viscosity oil (A3) that contains a volatile one in an amount of greater than or equal to 80 wt %, preferably greater than or equal to 90 wt %, more preferably greater than or equal to 95 wt %, based on the total weight, as 100 wt %, of A3.

According to the emulsion mentioned above, the low-viscosity oil (A3) and the silicone resins (A2) are used in a mass ratio of from 1 to 20, preferably from 2 to 10, more preferably from 3 to 8, most preferably from 4.5 to 7.

According to the emulsion mentioned above, the surfactant composition (B) is an alkyl alcohol polyether-based nonionic surfactant, preferably one, or a combination, of polyoxyethylene lauryl ether, polyoxyethylene cetyl ether, polyoxyethylene stearyl ether, iso-tridecanol polyoxyethylene ether, $C_{11}$-$C_{15}$ polyoxyethylene alkyl ether and polyoxyethylene oleyl ether.

According to the emulsion mentioned above, the surfactant composition (B) is one or more alkyl alcohol polyether-based nonionic surfactants, preferably one, or a combination, of polyoxyethylene lauryl ether, polyoxyethylene cetyl ether, polyoxyethylene stearyl ether, iso-tridecanol polyoxyethylene ether, $C_{11}$-$C_{15}$ polyoxyethylene alkyl ether and polyoxyethylene oleyl ether.

The emulsion mentioned above comprises the amino polyorganosiloxanes (A1), the silicone resins (A2) and the optional low-viscosity oil (A3), as well as the surfactant composition (B) characterized by containing iso-tridecanol polyoxyethylene ether and having a calculated average HLB value of from 12.5 to 13, preferably from 8 to 12, more preferably from 9 to 11.

The emulsion mentioned above comprises 10-20 wt % of one or more amino polyorganosiloxanes (A1), and/or 0.1-4 wt % of one or more silicone resins (A2), and/or 4-10 wt % of the surfactant composition (B), and water, based on the total weight, as 100 wt %, of the emulsion.

The emulsion mentioned above comprises one or more amino polyorganosiloxanes (A1) in an amount of from 10 to 20 wt %, preferably from 12 to 18 w %, based on the total weight, as 100 wt %, of the emulsion.

The emulsion mentioned above comprises one or more silicone resins (A2) in an amount of from 0.1 to 2 w %, preferably from 0.2 to 0.8 w %, more preferably from 0.3 to 0.7 w %, most preferably from 0.41 to 0.6 w %, based on the total weight, as 100 wt %, of the emulsion.

The emulsion mentioned above comprises the surfactant composition (B) in an amount of from 4 to 8 wt %, based on the total weight, as 100 wt %, of the emulsion.

According to the emulsion mentioned above, the optional low-viscosity oil (A3), which forms a system without phase separation with the amino polyorganosiloxanes (A1) and the silicone resins (A2), can be one or a mixture of more members selected from the group consisting of hydrocarbons, animal and vegetable oils, and organopolysiloxanes, preferably oligomeric polydialkylsiloxanes or cyclic polysiloxanes, more preferably volatile oligomeric linear organopolysiloxanes.

The use of emulsion mentioned above in leave-on or rinse-off hair care products, preferably in rinse-off hair care products.

The use of emulsion mentioned above in leave-on or rinse-off hair care products to make hairstyles hold, particularly on hair that has been treated by a permanent or temporary hair styling method, and preferably to maintain the degree of curling of the said hair.

According to the use mentioned above, the rinse-off hair care products are conditioners or hair masks, According to the use mentioned above, the leave-on hair care products are atmospheric-pressure hairstyling sprays.

The atmospheric-pressure hairstyling sprays herein generally comprise no propellant or compressed gas.

According to the use mentioned above, the leave-on hair care products are hairstyling gels.

The hairstyling gels herein are generally aqueous products that typically comprise less waxy ingredients, and have light texture, ease of spreading and low viscosity.

According to the use mentioned above, the leave-on hair care product comprising the aforesaid emulsion is applied to the hair to realize a temporary styling treatment thereon.

According to the use mentioned above, the leave-on hair care product comprising the aforesaid emulsion is applied to the dry hair that has been treated by a permanent or temporary hair styling method.

According to the use mentioned above, the rinse-off hair care product comprising the aforesaid emulsion is applied to the wet hair that are subsequently treated by a permanent or temporary hair styling method during and/or after a drying process.

According to the use mentioned above, the rinse-off hair care product comprising the aforesaid emulsion is applied to the wet hair and is then kept in contact with it for at least 1 minute. It is preferred to thermally treat the hair after this process.

The permanent hair styling herein for example with a chemical or hot perm mainly refers to a treatment method in which a reducing agent (including thioglycolic acid compounds) is used to break the cystine-disulfide bridges in the hair keratin to change the shape of the hair fibers, and then a fixative (including weak acids or peroxides) is used to close the cystine-disulfide bridge.

The temporary hair styling herein for example with a curling iron, hair dryer, flat iron or non-energized curler roll mainly refers to a treatment method for changing the hydrogen bond connection inside the hair fibers or on the hair surface by heat treatment and/or an external force.

As used herein, the term "amine number" refers to the amount of 1 N HCl required to neutralize the amino groups in 1 gram of amino compounds, measured in meq/g.

the amino polyorganosiloxanes (A1) in the oil-in-water emulsion of the present invention have an amine number of from 0.01 to 10.0 meq/g, preferably from 0.1 to 5.0 meq/g, and a viscosity of from 100 to 10,000 mPa·s measured at 25° C. according to DIN53019.

The hydroxyl and/or alkoxy groups of the amino polyorganosiloxanes (A1) crosslink with those of the silicone resins (A2). The closer the ratio of VIII is to 0, under the same other conditions, the more hydroxyl and alkoxy groups the amino polyorganosiloxanes (A1) contain, wherein the number of II or III could be obtained by $^{29}$Si NMR and $^{1}$H NMR.

The optional low-viscosity oil (A3) herein, which forms a system without phase separation with the amino polyorganosiloxanes (A1) and the silicone resins (A2), has a viscosity of less than 100 mm$^2$/s, more preferably less than 10 mm$^2$/s, most preferably less than 5 mm$^2$/s, measured according to DIN 51562, and can be selected from among hydrocarbons, animal and vegetable oils, and organopolysiloxanes that are oligomeric polydialkylsiloxanes or cyclic polysiloxanes. Preference is given to organopolysiloxanes with methyl groups attached to the silicon atoms; greater preference is given to low molecular weight oligomeric polydimethylsiloxanes or cyclic polydimethylsiloxanes, or oligomeric or cyclic polydimethylsiloxanes with other alkyl, aryl, alkaryl and aralkyl groups (for example, phenyl, benzyl and C$_1$-C$_{18}$ alkyl groups) as substituents; and the greatest preference is given to trimethylsilyl-terminated linear polydimethylsiloxanes having from 2 to 50 silicon atoms on average in the organopolysiloxane backbone inclusive of the trimethylsilyl end groups.

Further, preference is given to volatile organopolysiloxanes having an evaporation rate, measured in accordance with DIN53249, in the following ranges: as the volatile siloxane mixture evaporates, weight is reduced by 10-80% (preferably 20-70%) after 5 minutes and by 60-99.5% (preferably 70-90%) after 20 minutes, based on the total weight of the mixture before evaporating. The volatile organopolysiloxanes can be selected from among oligomeric linear organopolysiloxanes having at most about 3 to 7, preferably 5 to 6 silicon atoms in the backbone, and cyclic organopolysiloxanes having from 3 to 6 silicon atoms. The substituents attached to the silicon atoms of the oligomeric linear organopolysiloxanes can be aryl groups, C$_1$-C$_{18}$ alkyl groups, or functional groups which do not interfere with the stability of the resulting emulsion or its suitability to use in cosmetic formulations, preferably C$_{1-4}$alkyl groups, more preferably methyl groups. The cyclic organopolysiloxanes having from 3 to 6 silicon atoms are selected from hexamethylcyclotrisiloxane, octamethylcyclotetrasiloxane, decamethylcyclopentasiloxane, dodecamethylcyclohexasiloxane, and the like.

The oil phase herein is a mixture that comprises the amino polyorganosiloxanes (A1), the silicone resins (A2) and the optional low-viscosity oil (A3), not including the surfactant composition (B) and optional phenoxyethanol).

The calculated amine number of the oil phase=(weight of amino polyorganosiloxane α*amine number of amino polyorganosiloxane α+weight of amino polyorganosiloxane β*amine number of amino polyorganosiloxane β+weight of amino polyorganosiloxane γ*amine number of amino polyorganosiloxane γ+ . . . )/(weight of the oil phase).

The surfactant composition (B) employed in the present invention comprises one or more nonionic surfactants, ionic surfactants or amphoteric surfactants, preferably nonionic surfactants.

The nonionic surfactants herein are alkyl alcohol polyether, preferably fatty alcohol ethoxylates that typically contain the characteristic groups: —(OCH$_2$CH$_2$)$_m$OH, which are attached to aliphatic hydrocarbon groups having about 8 to 20 carbon atoms, such as lauryl (C$_{12}$), cetyl (C$_{16}$) and stearyl (C$_{18}$), where "m" may range from 1 to about 100, preferably from about 3 to 20. Common nonionic surfactants include one, or a combination, of polyoxyethylene lauryl ether, polyoxyethylene cetyl ether, polyoxyethylene stearyl ether, iso-tridecanol polyoxyethylene ether, C$_{11}$-C$_{15}$ polyoxyethylene alkyl ether and polyoxyethylene oleyl ether. These fatty alcohol ethoxylates are available as commercial products under trade names: ALFONIC®, BRIJ©, GENAPOL®, NEODOL®, SURFONIC®, TERGITOL©, TRYCOL®, SYMPATENS®, LUTENSOL® and the like.

The calculated average HLB value of the surfactant composition employed in the present invention=(HLB value of surfactant 1*weight of surfactant 1+HLB value of surfactant 2*weight of surfactant 2+ . . . )/(weight of surfactant 1+weight of surfactant 2+ . . . ).

According to the present invention, the calculated amine number of the oil phase formed from the amino polyorganosiloxanes (A1), the silicone resins (A2) and the optional low-viscosity oil (A3) ranges from 0.1 to 5.0 meq/g, and the calculated average HLB value of the surfactant composition (B) ranges from 10 to 15. Preferably, the calculated amine number of the oil phase ranges from 0.2 to 0.6 meq/g, more preferably from 0.23 to 0.29 meq/g, and the calculated average HLB value of the surfactant composition (B) ranges preferably from 12.5 to 13.

The oil-in-water emulsion of the present invention also comprises phenoxyethanol as a preservative in an amount of from 0 to 1 wt %, preferably from 0.5 to 1 wt %, based on the total weight of the emulsion.

A method for preparing the emulsion of the present invention comprising the steps of (1) well mixing the surfactant composition (B), the amino polyorganosiloxanes (A1), the silicone resins (A2), the optional low-viscosity oil (A3) and optional phenoxyethanol to form mixture (I) with a high-speed disperser or stirrer;

(2) slowly and uniformly adding an acid and/or aqueous solution thereof to mixture (I) while stirring to obtain mixture (II);

(3) uniformly adding water to the mixture from in step (2) to obtain a transparent oil-in-water emulsion; and (4) adjusting the pH value of the emulsion obtained in step (3) to 5.0-5.5 with an aqueous solution of NaOH.

In the above-mentioned method, the acid is a mineral or carboxylic acid that can be protonated with the amino groups in the amino polyorganosiloxanes (A1), wherein the mineral acid is selected from among hydrochloric, sulfuric and phosphoric acids, and the carboxylic acid is selected from among formic, acetic, propionic, citric, benzoic, oxalic and lactic acids, preferably acetic and formic acids.

DETAILED DESCRIPTION OF THE PREFERRED EMBODIMENTS

Unless otherwise specified, all parts and percentages in the examples are based on weight. Information on the components used in the examples is as follows:

Multiso 13/30, an iso-tridecanol polyoxyethylene ether (3 EO), with HLB=7.9, available from Sasol;

Multiso 13/120, an iso-tridecanol polyoxyethylene ether (12 EO), with HLB=14.5, available from Sasol;

Phenoxyethanol, available from Schulke;

Amino polyorganosiloxane 1, a side chain amino polyorganosiloxane terminated with hydroxyl and/or methoxy groups, having an amine number of 0.14 mmol/g and a viscosity of 5,000 mPa·s measured according to DIN 53019, where II/III=0 and the number of moles of the terminal hydroxyl groups is less than that of alkoxy groups, tested by $^{29}$Si NMR and $^1$H NMR;

Amino polyorganosiloxane 2, a side chain amino polyorganosiloxane terminated with hydroxyl and/or methoxy groups, having an amine number of 0.12 mmol/g and a viscosity of 5,000 mPa·s measured according to DIN 53019, where II/III=0 and the number of moles of the terminal hydroxyl groups is greater than that of alkoxy groups, tested by $^{29}$Si NMR and $^1$H NMR;

Amino polyorganosiloxane 3, WACKER® FINISH WR1300, a side chain amino polyorganosiloxane terminated with hydroxyl and/or methoxy groups, having an amine number of 0.3 mmol/g and a viscosity of 1,000 mPa·s measured according to D IN 53019, where II/III=0.

The above amino polyorganosiloxanes are supplied by WACKER CHEMIE AG.

Low-viscosity silicone fluid 1, BELSIL® DM2, having a viscosity of 2 mm²/s measured according to DIN 51562, available from WACKER CHEMIE AG;

Low-viscosity silicone fluid 2, BELSIL® 0.65, having a viscosity of 0.65 mm²/s measured according to DIN 51562, available from WACKER CHEMIE AG;

BELSIL® TM 803, a white solid powder at room temperature and MQ silicone resin with an Mw of 7300 g/mol, all units selected from VII and X, where alkoxy and hydroxyl groups are present in a total amount of 3.3 wt % and the hydroxyl content is less than or equal to 0.3 wt %, based on the total weight of silicone resins, available from WACKER CHEMIE AG;

BELSIL® MK Powder, a white solid powder at room temperature and T-type silicone resin with methoxy and methyl functional groups, all units selected from IX, having an Mw of about 10,000 g/mol;

SILRES® MSE 100, a liquid at room temperature and oligomeric T-type silicone resin with methoxy and methyl functional groups, all units selected from IX, having a solvent content of less than 2%, an Mw of from 2,000 to 5,000 g/mol and a viscosity of from 20 to 35 mm²/s;

SILRES® IC368, a solvent-free liquid at room temperature and oligomeric T-type silicone resin with methoxy, methyl and phenyl functional groups, all units selected from IX, wherein the content of methoxy groups is 15 wt % and the molar ratio of phenyl to methoxy is 1, having an active substance content of 84%, an Mw of about 1,900 g/mol and a viscosity of from 280 to 320 mm²/s;

The above silicone resins are supplied by WACKER CHEMIE AG.

TABLE 1

|  | Silicone resins (A2) (wt %) | | BELSIL® DM2 (wt %) | BELSIL® 0.65 (wt %) | Amino poly-organo-siloxane 1 (wt %) | Evaluation |
|---|---|---|---|---|---|---|
| 1 | BELSIL TM 803 | 1 | 5 | | | transparent |
| 2 | SILRES MSE 100 | 1 | 5 | | | transparent |
| 3 | SILRES IC368 | 1 | 5 | | | transparent |
| 4 | BELSIL MK | 1 | 5 | | | insoluble, powder deposited on the bottom |
| 5 | BELSIL MK | 1 | | 5 | | transparent |
| 6 | BELSIL TM 803 | 1 | 5 | | 38 | transparent |
| 7 | SILRES MSE 100 | 1 | 5 | | 38 | / |
| 8 | SILRES IC368 | 1 | 5 | | 38 | very turbid |
| 9 | BELSIL MK | 1 | 5 | | 38 | / |
| 10 | BELSIL MK | 1 | | 5 | 38 | translucent |

Compatibility test herein refers to a test in which the substances were mixed at room temperature as shown in Table 1, and after 24 hours the compatibility was observed.

Preparation Method

The following examples and comparative examples were carried out at room temperature according to the ratios of the ingredients shown in Table 2.

(1) the surfactant composition, the polyorganosiloxanes, the silicone resins, the optional low-viscosity oil and phenoxyethanol were mixed to form mixture (I) with IKA Eurostar 60 Digital (800-1500 rpm) stirrer;

(2) an aqueous acetic acid solution (containing acetic acid and water) was slowly added to mixture (I) while being stirred to obtain mixture (II).

(3) the remaining water was uniformly added to the mixture from step (2) to obtain a transparent oil-in-water emulsion; and (4) the pH value of the emulsion obtained in step (3) was adjusted to 5-5.5 with 10 wt % aqueous solution of NaOH.

The compositions used in the examples and comparative examples are shown in Table 2, and the test results are shown in Table 4.

TABLE 2

| | C. Ex. 0 | Ex. 1 | Ex. 2 | Ex. 3 | Ex. 4 | Ex. 5 | Ex. 6 | Ex. 7 | C. Ex. 8 | C. Ex. 9 | Ex. 10 | C. Ex. 11 | C. Ex. 12 |
|---|---|---|---|---|---|---|---|---|---|---|---|---|---|
| Multiso 13/30 | 4.5 | 4.5 | 4.5 | 4.5 | 4.5 | 4.5 | 4.5 | 4.5 | 4.5 | 4.5 | 4.5 | 4.5 | 4.5 |
| Multiso 13/120 | 2 | 2 | 2 | 2 | 2 | 2 | 2 | 2 | 2 | 2 | 2 | 2 | 2 |
| Phenoxyethanol | 1 | 1 | 1 | 1 | 1 | 1 | 1 | 1 | 1 | 1 | 1 | 1 | 1 |
| Amino polyorgano-siloxane 1 | 16 | 16 | 16 | 16 | | 16 | 16 | 16 | 16 | 16 | 16 | 16 | |
| Amino polyorgano-siloxane 2 | | | | | 16 | | | | | | | | |
| Amino polyorgano-siloxane 3 | | | | | | | | | | | | | 16 |
| BELSIL TM 803 | / | 1.78 | 0.64 | 0.42 | 0.42 | 0.32 | 0.23 | 0.21 | | | | | 0.42 |
| BELSIL ® MK | / | | | | | | | | 0.21 | 0.42 | | | |
| SILRES ® MSE100 | / | | | | | | | | | | 0.42 | | |
| SILRES ® IC 368 | / | | | | | | | | | | | 0.42 | |
| BELSIL DM 2 | 2.11 | 8.9 | 3.2 | 2.11 | 2.11 | 1.6 | 1.14 | 2.11 | 2.11 | | 2.11 | 2.11 | 2.11 |
| BELSIL 0.65 | | | | | | | | | | 2.11 | | | |
| Acetate Acid solution | 10.15 | 10.15 | 10.15 | 10.15 | 10.15 | 10.15 | 10.15 | 10.15 | 10.15 | 10.15 | 10.15 | 10.15 | 10.15 |
| Water | 64.24 | 55.67 | 62.51 | 63.82 | 63.82 | 64.43 | 64.98 | 63.82 | 63.82 | 63.82 | 63.82 | 63.82 | 63.82 |
| total | 100 | 100 | 100 | 100 | 100 | 100 | 100 | 100 | 100 | 100 | 100 | 100 | 100 |

Film-Forming Experiment 3 g of the transparent emulsions of examples and comparative examples were respectively spread on an A1 foil tart cups having a radius of 7.7 cm, and stored for drying at 25° C. and 70% r.h for 96 hours. Afterwards, a scraper was used to scratch the film and the degree of film formation is rated (see Table 3).

TABLE 3

| | | | Rating System | | |
|---|---|---|---|---|---|
| Scoring | 0 | 1 | 2 | 3 | 5 |
| Observed results | Significant wire drawing | Solid film broken but no wire drawing | Solid film intact Significant scratches on film surface | Solid film intact Slight scratches on film surface | Solid film intact No scratches on film surface |

In Table 3, the higher the score, the higher the degree of crosslinking.

TABLE 4

| | C. Ex. 0 | Ex. 1 | Ex. 2 | Ex. 3 | Ex. 4 | Ex. 5 | Ex. 6 | Ex. 7 | C. Ex. 8 | C. Ex. 9 | Ex. 10 | C. Ex. 11 | C. Ex. 12 |
|---|---|---|---|---|---|---|---|---|---|---|---|---|---|
| Score | No film formed | 5 | 5 | 3 | 5 | 3 | 1 | 1 | 0 | 0 | 2 | 1 | 1 |

In C.Ex.12, the viscosity of the amino polyorganosiloxane was too low to form a film having a high degree of crosslinking and a high score.

In C.Ex.8 and 9, in spite of a silicone resin with a higher Mw used, a film having a high degree of crosslinking and a high score was not formed yet. In contrast, through the Mw of the silicone resin used in Ex.10 is lower than that of the silicone resin used in C.Ex.8, a film having a higher score was formed.

The inventors of the present invention surprisingly found that, if II/III=0, when the amino polyorganosiloxanes (A1) having a higher viscosity and a higher molecular weight were used in combination with a solid MQ type silicone resin, a film having a high degree of crosslinking and a high score could be formed. Moreover, when the silicone resins (A2), the amino polyorganosiloxanes (A1) and the low viscosity oil (A3) were mixed to form a transparent homogeneous phase, a solid film having a higher strength and a higher score can be formed.

Hair Curl Test

The hair tresses (10 g, 20 cm) were washed with ether and then with a 5% ammonium lauryl sulfate solution. The hair tresses were completely wet with water. Afterwards, 0.7 ml of the sample was evenly applied to each tress, which was fully rubbed for 30 seconds, let stand for 30 seconds before rinsing with 35° C. warm water, and hung on the hair rack for air-drying for later use.

Basic Formulation of Conditioner

| Phase | Grade | INCI | wt % |
|---|---|---|---|
| A | | Water | q.s. to 100 |
| | | Glycerol | 3.00 |
| | Natrosol 250HHR | Hydroxyethyl cellulose | 1.50 |
| | | Disodium EDTA | 0.10 |
| B | Genamin KDMP | Docosyltrimethylammonium chloride | 2.00 |
| | Lanette O | Cetearyl alcohol | 5.00 |
| C | Microcare IT | Isothiazolinone | 0.10 |
| D | | Water + emulsion of examples | 10.00 |

The amino polyorganosiloxanes (A1) and the silicone resins (A2) are present in the conditioner in a total amount of 1.5 wt %, based on the total weight, as 100 wt %, of the basic formulation of the conditioner.

A conditioner sample was applied, at 0.5 g per 1.5 g of hair, to the prepared hair tress wetted again with water, which was rubbed for 1 minute and let stand for 1 minute before rinsing with water for 30 seconds. The water was absorbed from the hair tress with a paper towel until no water drips. At 25° C. and 70% r.h., a curling iron was heated to and maintained at 170° C. The hair tress was wound 4 turns clockwise around a curling iron, and after 15 to 20 seconds let naturally relax to cool down at room temperature.

The hair tress was placed vertically, with the top end fixed, photographed and scored to obtain the initial degree of curling.

A spray bottle was used to spray water onto the upper, middle and lower parts of the aforesaid hair tress once, which was immediately combed twice from top to bottom with a plastic comb, and air-dried. The hair tress was photographed again and scored to obtain the final degree of curling. The initial and final degrees of curling were compared and scored in terms of tress length change, number of curls, and angle change.

TABLE 5

| | C. Ex. 0 | Ex. 2 | Ex. 3 | Ex. 4 | C. Ex. 8 | C. Ex. 12 |
|---|---|---|---|---|---|---|
| Hairstyle's hold (degree of curling evaluation) | Average | Good | Good | Very good | Average | Average |
| Storage stability at 48° C. (d) | / | 21 | 28 | 3 | 3 | 28*2 |
| Soft | 2 | 0 | 1 | 0 | 1 | 2 |
| Sticky | 1 | 3 | 2 | 3 | 3 | 2 |

The inventors of the present invention surprisingly found that, if the conditioner comprised an emulsion having a high degree of crosslinking and a good film strength, the hair tress treated with this conditioner exhibited a good style's hold, and had a smooth, non-sticky hand feel.

Each hair tress was touched by a 9-person test panel to evaluate its softness and smoothness. Results were classified into 3 grades: 0=fair, 1=good, 2=very good.

In Table 5 above, the stickiness (hand feel) was evaluated in reference to the following:

The stickiness of lanolin wax was given 10 points (very sticky);

Jergens Aloe and Lanolin (commercial product) oil-in-water lotion was given 5 points (moderately sticky);

The stickiness of baby oil (pure mineral oil) was given 0 point (not significantly sticky).

The invention claimed is:

1. A film-forming oil-in-water emulsion, comprising:

one or more amino polyorganosiloxanes (A1), one or more silicone resins (A2), a surfactant composition (B) and water;

wherein at least 80 mol % of units of the amino polyorganosiloxanes (A1) are selected from those having the following general formulas Ia, Ib II and III:

$$R^1_2SiO_{(4-a-b)/2} \tag{Ia}$$

$$R^1_aR^2_bSiO_{(4-a-b)/2} \tag{Ib}$$

$$R^3_3SiO_{(1/2)} \tag{II}$$

$$R^3_2R^4SiO_{(1/2)} \tag{III}$$

wherein a has the value 0 or 1;

wherein b has the value 1 or 2;

wherein a+b is equal to 2;

wherein $R^1$ represents monovalent hydrocarbon groups having 1-40 carbon atoms;

wherein $R^2$ represents aminoalkyl groups of the general formula IV:

$$—R^5—NR^6R^7 \tag{IV}$$

wherein $R^5$ represents divalent hydrocarbon groups having 1-40 carbon atoms;

wherein $R^6$ represents divalent hydrocarbon groups having 1-40 carbon atoms, H, hydroxymethyl or alkanoyl;

wherein $R^7$ represents groups of the general formula V:

$$\text{——}(R^8\text{——}NR^6)_x R^6 \qquad (V)$$

wherein x is 0 or an arbitrary integer from 1 to 40;
wherein $R^8$ represents divalent groups of the general formula VI:

$$\text{——}(CR^9_2\text{——})_y \qquad (VI)$$

wherein y an arbitrary integer from 1 to 6;
wherein $R^9$ represents H or hydrocarbon groups having 1-40 carbon atoms;
wherein $R^3$ represents optionally halogen-substituted hydrocarbon groups having 1-40 carbon atoms;
wherein $R^4$ represents —OR or —OH groups;
wherein (Ia+Ib)/(II+III), meaning the average ratio of the sum of units of the general formulas Ia and Ib to the sum of units of the general formulas II and III, ranges from 0.5 to 1000, wherein II/III≤1;
wherein the amino polyorganosiloxanes (A1) have a viscosity of from 5,000 to 9,000 mPa's measured at 25° C. according to DIN53019;
wherein at least 80 mol % of units of the silicone resins (A2) are selected from those having the following general formulas VII, VIII, IX and X:

$$R^{10}_3 SiO_{(1/2)} \qquad (VII)$$
$$R^{10}_2 SiO_{(2/2)} \qquad (VIII)$$
$$R^{10} SiO_{(3/2)} \qquad (IX)$$
$$SiO_{(4/2)} \qquad (X)$$

wherein $R^{10}$ represents hydrocarbon groups that have 1-40 carbon atoms and are optionally substituted by halogens, or H, —OR or —OH groups;
wherein at least 20 mol % of the units are selected from those having the general formulas IX and X,
wherein at most 30 wt % of $R^{10}$ are —OR and/or —OH groups, based on the total weight of the silicone resins (A2);
wherein in the terminal groups of the amino polyorganosiloxanes (A1), the number of moles of hydroxyl groups is greater than that of alkoxy groups; and
wherein the emulsion is used in leave-on or rinse-off hair care products to make hairstyles hold or to maintain the degree of curling of the said hair.

2. The film-forming oil-in-water emulsion of claim 1, further comprising a low-viscosity oil (A3) that contains a volatile one in an amount of greater than or equal to 90 wt %; and
wherein the low-viscosity oil (A3) has a viscosity of less than 100 mm²/s, measured according to DIN 51562 at 25° C.

3. The film-forming oil-in-water emulsion of claim 2, wherein the silicone resins (A2), the amino polyorganosiloxanes (A1) and the low viscosity oil (A3) were mixed to form a transparent homogeneous phase.

4. The film-forming oil-in-water emulsion of claim 2, wherein the low-viscosity oil (A3) and the silicone resins (A2) are used in a mass ratio of from 1 to 20.

5. The film-forming oil-in-water emulsion of claim 1, comprising:
  10-20 wt % of one or more amino polyorganosiloxanes (A1), and/or 0.1-4 wt % of one or more silicone resins (A2), and/or 4-10 wt % of the surfactant composition (B), and water, based on the total weight, as 100 wt %, of the emulsion.

6. The film-forming oil-in-water emulsion of claim 1, wherein the silicone resins (A2) comprise at least 80 mol % of units are selected from those having the general formulas VII and X, based on the total units, as 100 mol % of, the silicone resins (A2).

7. The film-forming oil-in-water emulsion of claim 1, comprising one or more silicone resins (A2) in an amount of from 0.1 to 2 wt % based on the total weight, as 100 wt %, of the emulsion.

8. The film-forming oil-in-water emulsion of claim 1, wherein the rinse-off hair care products are conditioners or hair masks.

9. The film-forming oil-in-water emulsion of claim 1, wherein the leave-on hair care products are atmospheric-pressure hairstyling sprays or hairstyling gels.

10. The film-forming oil-in-water emulsion of claim 1, wherein the leave-on hair care product is applied to the hair to realize a temporary styling treatment thereon; or
  wherein the leave-on hair care product is applied to dry hair that has been treated by a permanent or a temporary hair styling method.

11. The film-forming oil-in-water emulsion of claim 1, wherein the rinse-off hair care product is applied to wet hair that are subsequently treated by a permanent or a temporary hair styling method during and/or after a drying process.

12. The film-forming oil-in-water emulsion of claim 1, wherein the rinse-off hair care product is applied to wet hair and is then kept in contact with it for at least 1 minute.

13. The film-forming oil-in-water emulsion of claim 1, wherein in amino polyorganosiloxanes (A1), II/III≤0.3.

14. The film-forming oil-in-water emulsion of claim 2, wherein the mass ratio of the low-viscosity oil (A3) to the silicone resins (A2) is from 1 to 20.

15. The film-forming oil-in-water emulsion of claim 1, wherein the one or more silicone resins (A2) are present in an amount of from 0.3 to 0.7 wt %, based on the total weight, as 100 wt %, of the emulsion.

16. (+) The film-forming oil-in-water emulsion of claim 1, wherein the one or more silicone resins (A2) are an MQ type resin having units selected from the general formulas VII and X and alkoxy and hydroxyl groups are present in a total amount of 3.3 wt % and the hydroxyl content is less than or equal to 0.3 wt %, based on the total weight of silicone resins.

17. A film-forming oil-in-water emulsion, comprising:
  one or more amino polyorganosiloxanes (A1), one or more silicone resins (A2), a surfactant composition (B) and water;

wherein at least 80 mol % of units of the amino polyorganosiloxanes (A1) are selected from those having the following general formulas Ia, Ib II and III:

$$R^1_2SiO_{(4-a-b)/2} \tag{Ia}$$

$$R^1_aR^2_bSiO_{(4-a-b)/2} \tag{Ib}$$

$$R^3_3SiO_{(1/2)} \tag{II}$$

$$R^3_2R^4SiO_{(1/2)} \tag{III}$$

wherein a has the value 0 or 1;

wherein b has the value 1 or 2;

wherein a+b is equal to 2;

wherein $R^1$ represents monovalent hydrocarbon groups having 1-40 carbon atoms;

wherein $R^2$ represents aminoalkyl groups of the general formula IV:

$$\text{---}R^5\text{---}NR^6R^7 \tag{IV}$$

wherein $R^5$ represents divalent hydrocarbon groups having 1-40 carbon atoms;

wherein $R^6$ represents divalent hydrocarbon groups having 1-40 carbon atoms, H, hydroxymethyl or alkanoyl;

wherein $R^7$ represents groups of the general formula V:

$$\text{---}(R^8\text{---}NR^6)_xR^6 \tag{V}$$

wherein x is 0 or an arbitrary integer from 1 to 40;

wherein $R^8$ represents divalent groups of the general formula VI:

$$\text{---}(CR^9_2\text{---})_y \tag{VI}$$

wherein y an arbitrary integer from 1 to 6;

wherein $R^9$ represents H or hydrocarbon groups having 1-40 carbon atoms;

wherein $R^3$ represents optionally halogen-substituted hydrocarbon groups having 1-40 carbon atoms;

wherein $R^4$ represents ---OR or ---OH groups;

wherein (Ia+Ib)/(II+III), meaning the average ratio of the sum of units of the general formulas Ia and Ib to the sum of units of the general formulas II and III, ranges from 0.5 to 1000, wherein II/III≤1;

wherein the amino polyorganosiloxanes (A1) have a viscosity of from 4,000 to 6,000 mPa's measured at 25° C. according to DIN53019;

wherein at least 80 mol % of units of the silicone resins (A2) are selected from those having the following general formulas VII, VIII, IX and X:

$$R^{10}_3SiO_{(1/2)} \tag{VII}$$

-continued $$R^{10}_2SiO_{(2/2)} \tag{VIII}$$

$$R^{10}SiO_{(3/2)} \tag{IX}$$

$$SiO_{(4/2)} \tag{X}$$

wherein $R^{10}$ represents hydrocarbon groups that have 1-40 carbon atoms and are optionally substituted by halogens, or H, ---OR or ---OH groups;

wherein at least 20 mol % of the units are selected from those having the general formulas IX and X, wherein at most 30 wt % of $R^{10}$ are ---OR and/or ---OH groups, based on the total weight of the silicone resins (A2);

wherein in the terminal groups of the amino polyorganosiloxanes (A1), the number of moles of hydroxyl groups is greater than that of alkoxy groups; and wherein the emulsion is used in leave-on or rinse-off hair care products to make hairstyles hold or to maintain the degree of curling of the said hair.

18. A film-forming oil-in-water emulsion, comprising:

one or more amino polyorganosiloxanes (A1), one or more silicone resins (A2), a low-viscosity oil (A3), a surfactant composition (B) and water;

wherein at least 80 mol % of units of the amino polyorganosiloxanes (A1) are selected from those having the following general formulas Ia, Ib II and III:

$$R^1_2SiO_{(4-a-b)/2} \tag{Ia}$$

$$R^1_aR^2_bSiO_{(4-a-b)/2} \tag{Ib}$$

$$R^3_3SiO_{(1/2)} \tag{II}$$

$$R^3_2R^4SiO_{(1/2)} \tag{III}$$

wherein a has the value 0 or 1;

wherein b has the value 1 or 2;

wherein a+b is equal to 2;

wherein $R^1$ represents monovalent hydrocarbon groups having 1-40 carbon atoms;

wherein $R^2$ represents aminoalkyl groups of the general formula IV:

$$\text{---}R^5\text{---}NR^6R^7 \tag{IV}$$

wherein $R^5$ represents divalent hydrocarbon groups having 1-40 carbon atoms;

wherein $R^6$ represents divalent hydrocarbon groups having 1-40 carbon atoms, H, hydroxymethyl or alkanoyl;

wherein $R^7$ represents groups of the general formula V:

$$\text{---}(R^8\text{---}NR^6)_xR^6 \tag{V}$$

wherein x is 0 or an arbitrary integer from 1 to 40;

wherein $R^8$ represents divalent groups of the general formula VI:

5

$$—(CR^9{}_2—)_y \qquad \text{(VI)}$$

10

15 wherein y an arbitrary integer from 1 to 6;

wherein $R^9$ represents H or hydrocarbon groups having 1-40 carbon atoms;

wherein $R^3$ represents optionally halogen-substituted hydrocarbon groups having 1-40 carbon atoms;

wherein $R^4$ represents —OR or —OH groups;

wherein (Ia+Ib)/(II+III), meaning the average ratio of the sum of units of the general formulas Ia and Ib to the sum of units of the general formulas II and III, ranges from 0.5 to 1000, wherein II/III≤1;

wherein the amino polyorganosiloxanes (A1) have a viscosity of from 3,000 to 9,000 mPa's measured at 25° C. according to DIN53019;

wherein at least 80 mol % of units of the silicone resins (A2) are selected from those having the following general formulas VII, VIII, IX and X:

$$R^{10}{}_3SiO_{(1/2)} \qquad \text{(VII)}$$

$$R^{10}{}_2SiO_{(2/2)} \qquad \text{(VIII)}$$

wherein $R^{10}$ represents hydrocarbon groups that have 1-40 carbon atoms and are optionally substituted by halogens, or H, —OR or —OH groups;

wherein at least 20 mol % of the units are selected from those having the general formulas IX and X, wherein at most 30 wt % of $R^{10}$ are —OR and/or —OH groups, based on the total weight of the silicone resins (A2);

wherein in the terminal groups of the amino polyorganosiloxanes (A1), the number of moles of hydroxyl groups is greater than that of alkoxy groups;

wherein the low-viscosity oil (A3) contains a volatile one in an amount of greater than or equal to 90 wt % and a viscosity of less than 100 mm²/s, measured according to DIN 51562 at 25° C.; and wherein the mass ratio of the low-viscosity oil (A3) to the silicone resins (A2) is from 5 to 20; wherein the emulsion is used in leave-on or rinse-off hair care products to make hairstyles hold or to maintain the degree of curling of the said hair.

\* \* \* \* \*

20

25